United States Patent
Coates et al.

(10) Patent No.: US 7,716,752 B2
(45) Date of Patent: May 18, 2010

(54) PROTECTIVE UNDERGARMENT CONFIGURED FOR IMPROVED HANDLING

(75) Inventors: Fredrica V. Coates, Winston-Salem, NC (US); Donald A. Sheldon, Downingtown, PA (US)

(73) Assignee: First Quality Retail Services, LLC, Great Neck, NY (US)

( * ) Notice: Subject to any disclaimer, the term of this patent is extended or adjusted under 35 U.S.C. 154(b) by 776 days.

(21) Appl. No.: 10/484,024

(22) PCT Filed: Jul. 18, 2002

(86) PCT No.: PCT/US02/22703

§ 371 (c)(1),
(2), (4) Date: Aug. 20, 2004

(87) PCT Pub. No.: WO03/007865

PCT Pub. Date: Jan. 30, 2003

(65) Prior Publication Data

US 2005/0022291 A1  Feb. 3, 2005

Related U.S. Application Data

(60) Provisional application No. 60/305,897, filed on Jul. 18, 2001.

(51) Int. Cl.
*A41B 9/00* (2006.01)

(52) U.S. Cl. .................. 2/400; 2/402; 604/39

(58) Field of Classification Search .............. 2/402, 2/408, 400, 401; 604/39
See application file for complete search history.

(56) References Cited

U.S. PATENT DOCUMENTS

| | | | | |
|---|---|---|---|---|
| 1,188,223 A * | 6/1916 | Uyeda | ............ | 604/394 |
| 1,195,904 A * | 8/1916 | Bornstein | ............ | 2/402 |
| 2,492,265 A * | 12/1949 | Bryan | ............ | 2/402 |
| 4,051,854 A * | 10/1977 | Aaron | ............ | 604/394 |
| 4,675,918 A * | 6/1987 | O'Brien | ............ | 2/402 |
| 4,995,873 A * | 2/1991 | Knight | ............ | 604/391 |
| 5,069,678 A * | 12/1991 | Yamamoto et al. | ............ | 604/385.21 |
| 5,209,743 A * | 5/1993 | Hardison | ............ | 604/391 |
| 5,261,901 A * | 11/1993 | Guay | ............ | 604/391 |
| 5,873,870 A * | 2/1999 | Seitz et al. | ............ | 604/385.04 |
| 6,125,476 A * | 10/2000 | Jerome | ............ | 2/403 |

OTHER PUBLICATIONS

International Search Report, Application No. PCT/US/02/22703, dated Nov. 11, 2002.

* cited by examiner

*Primary Examiner*—Katherine Moran
*Assistant Examiner*—Richale L Quinn
(74) *Attorney, Agent, or Firm*—Amster, Rothstein & Ebenstein LLP

(57) ABSTRACT

A protective undergarment is provided according to exemplary aspects of this invention. The undergarment includes a waist portion adapted to encircle the waist of a user. The undergarment also includes a crotch portion having an end segment extending from the waist portion, a central segment, and a terminal end segment attachable to the waist portion. The terminal end segment of the crotch portion extends substantially perpendicular to the waist portion.

16 Claims, 10 Drawing Sheets

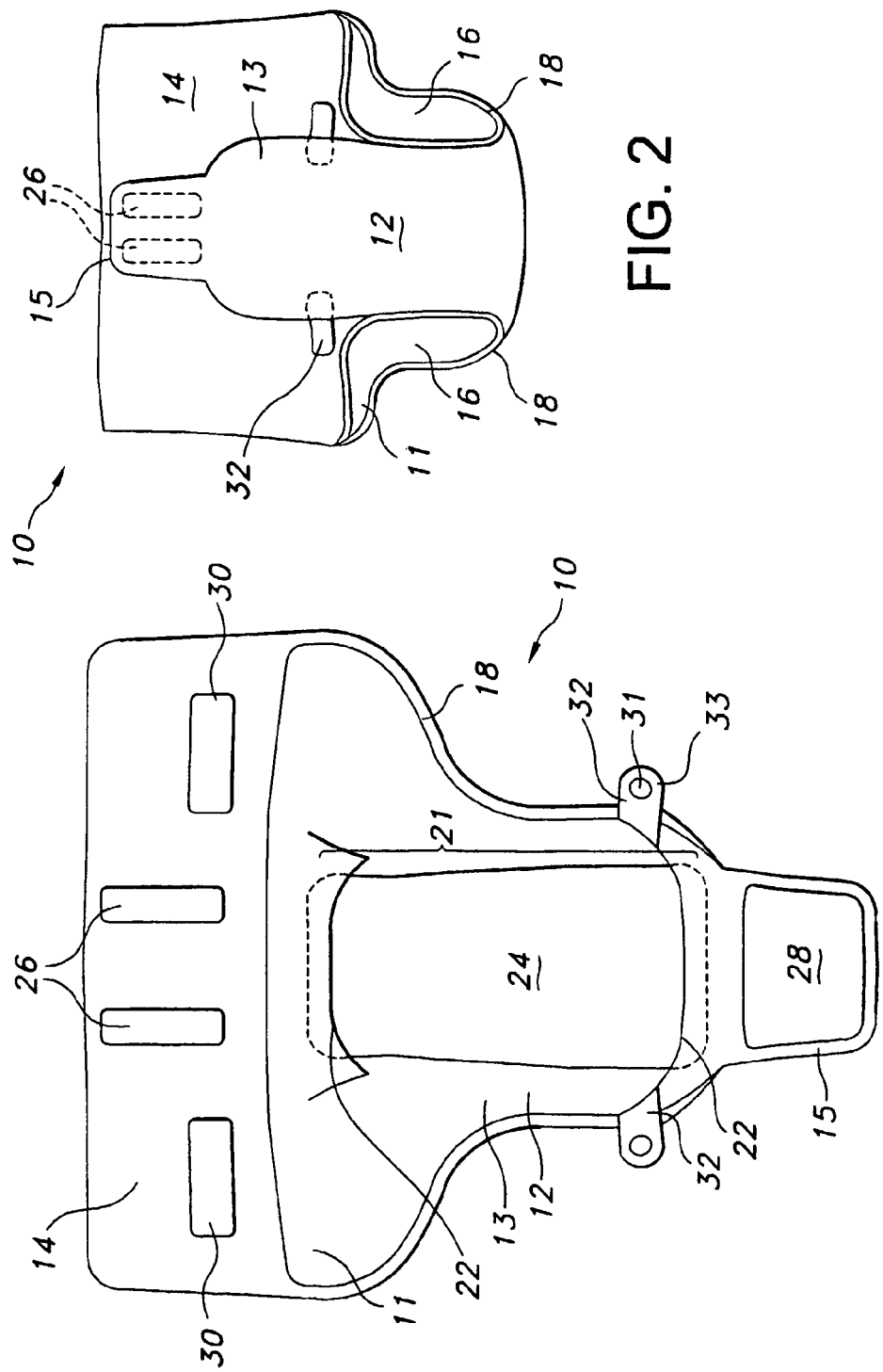

PROTECTIVE UNDERGARMENT CONFIGURED FOR IMPROVED HANDLING

CROSS REFERENCE TO RELATED APPLICATION

This is a U.S. National Phase of International Application No. PCT/US02/22703 filed Jul. 18, 2002.

This application claims priority of U.S. Provisional Patent Application No. 60/305,897 by Fredrica Coates, filed Jul. 18, 2001, titled UNISEX STRETCH PROTECTIVE UNDERWEAR, which is incorporated herein by reference.

FIELD OF THE INVENTION

This invention relates to protective undergarments. More specifically, it relates to protective undergarments configured for improved handling, such as those for wheelchair-bound or bedridden patients.

BACKGROUND OF THE INVENTION

The use of absorbent articles, such as protective undergarments, has increased steadily for many years. Early uses, such as diapers for babies and sanitary products for women, have in recent years been joined by an increasing demand for products designed to deal with incontinence issues for adults, frequently brought on by advanced age, obesity, or a variety of medical conditions. At the same time, markets have grown in all of these areas for both disposable and reusable products, depending on the preferences of the consumer.

Disposable absorbent articles, such as diapers and pads for example, are in widespread use throughout the world as a result of their convenience. They provide substantial advantages and convenience over absorbent articles that have to be laundered and reused, particularly when the absorbent articles are used away from home. In recent years, many different disposable absorbent articles have been proposed and some have been very successful in the marketplace. However, even current successful products leave room for improvement.

To promote preservation of the environment, some consumers desire to return to the use of reusable, rather than disposable, absorbent articles such as infant and adult diapers. A recent improvement to reusable diapers is in the replacement of pin fasteners by fasteners of filamentary material, such as hook and loop filamentary materials manufactured by Velcro Corporation and Aplix Corporation. In this regard, reference is made to U.S. Pat. No. 4,537,591 to Coates, incorporated herein by reference, which discloses a cloth diaper having filamentary fasteners together with a self-closing tab cover that protects the fasteners from buildup of lint during washing.

Whether for reusable or disposable products, various fastening systems have been employed for fastening the absorbent products to the wearer or to the clothing of the wearer. For example, the waistband of a diaper is preferably fastened around the waist of the wearer, and the fastening system is generally intended to hold the diaper in snug encircling fashion on the wearer's torso. After the diaper is soiled, it is removed by unfastening the tabs, thereby opening the waist.

The configuration of reusable and/or disposable products for adults, especially the infirm or obese, and/or those with limited dexterity, is additionally made difficult by the size and weight of the person wearing the garment. These factors hinder the donning and doffing of protective undergarments having traditional configurations. For example, it is extremely inconvenient for a caregiver to be required to remove an undergarment just to see if a change is needed, particularly if the undergarment is being worn by a large and/or immobile person. Thus there continues to be a need for undergarments affording easier access for checking, and greater facility of donning and doffing.

SUMMARY OF THE INVENTION

A protective undergarment is provided according to exemplary aspects of this invention. The undergarment includes a waist portion adapted to encircle the waist of a user. The undergarment also includes a crotch portion having an end segment extending from the waist portion, a central segment, and a terminal end segment attachable to the waist portion. The terminal end segment of the crotch portion extends substantially perpendicular to the waist portion.

According to another aspect of this invention, a protective undergarment is provided including a waist portion adapted to encircle the waist of a user, wherein the waist portion comprises end segments. The protective undergarment also includes a crotch portion comprising an end segment extending from the waist portion, a central segment, and a terminal end segment attachable to the waist portion. The terminal end segment extends substantially perpendicular to the waist portion, and the terminal end segment of the crotch portion is no wider than the central segment. Each of the end segments of the waist portion is configured for engagement to at least one of the terminal end segment of the crotch portion and the other of the end segments of the waist portion. Upon engagement, the end segments of the waist portion and the terminal end segment of the crotch portion engage one another in a common region.

BRIEF DESCRIPTION OF DRAWINGS

The invention is best understood from the following detailed description when read in connection with the accompanying drawings. It is emphasized that, according to common practice, the various features of the drawings are not rendered to any particular proportion or scale. On the contrary, the dimensions of the various features are arbitrarily expanded or reduced for clarity. Included in the drawings are the following figures:

FIG. 1 is a front view of an exemplary embodiment of the present invention showing the undergarment open in the position that would allow a caregiver to change the pad or check to see if the pad needs changing.

FIG. 2 is a view of the undergarment of FIG. 1, as it would be worn.

DETAILED DESCRIPTION OF THE INVENTION

Figure 3:
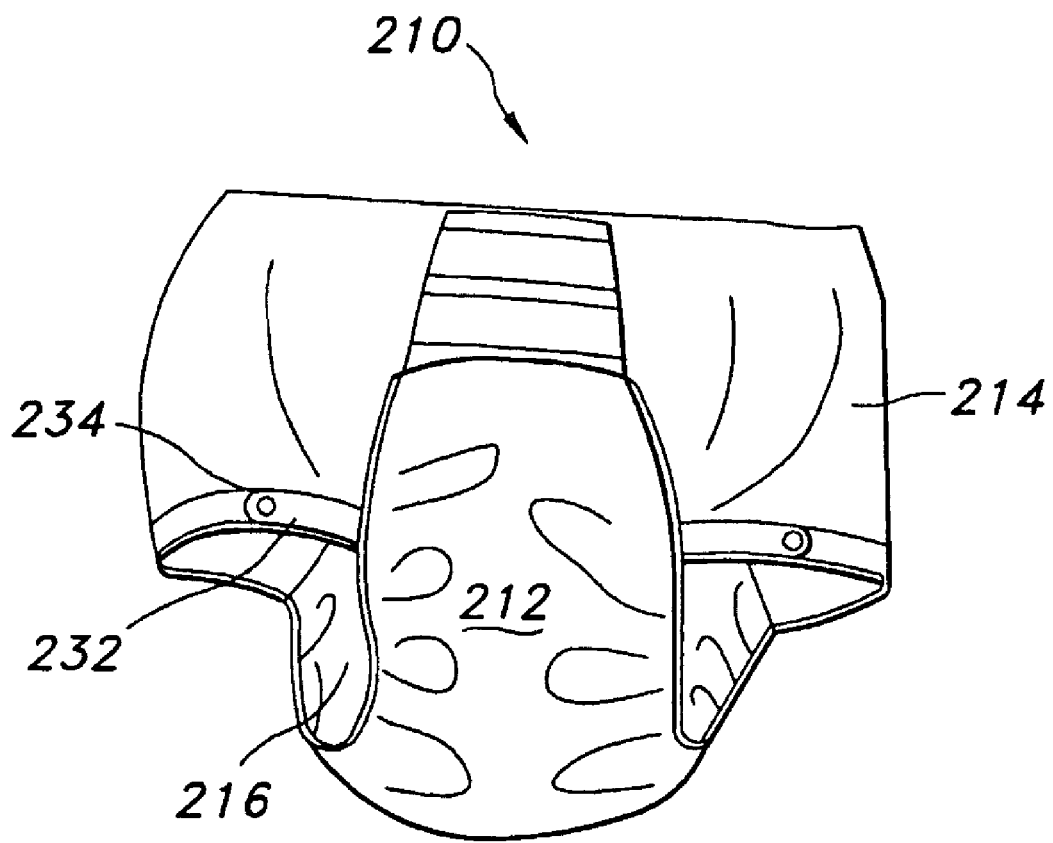
FIG. 3 is a view of another exemplary embodiment of the invention, comprising snaps for leg closures, as the garment would be worn.

Exemplary features of selected embodiments of this invention will now be described with reference to the figures. It will be appreciated that the spirit and scope of the invention is not limited to the embodiments selected for illustration. It is contemplated that any of the configurations and materials described hereafter can be modified within the scope of this invention.

Referring to the figures generally, a protective undergarment, such as undergarments 10, 210, 310, 410, 510, 610, 710, 810, and 910, is provided. The undergarment 10, for example, includes a waist portion 14 adapted to encircle the waist of a user. The undergarment 10 also includes a crotch portion 12 comprising an end segment 11 extending from the waist portion 14, a central segment 13, and a terminal end segment 15 attachable to the waist portion 14. The terminal end segment 15 extends substantially perpendicular to the waist portion 14.

The waist portion 14 of the protective undergarment 10 optionally includes end segments (such as end segments 838, 840 in FIG. 9) each being configured for engagement to at least one of the terminal end segment 15 of the crotch portion 12 and the other of the end segments of the waist portion 14. Upon engagement, the optional end segments of the waist portion 14 and the terminal end segment 15 of the crotch portion 12 engage one another in a common region.

Each of the end segments of the waist portion 14 and the terminal end segment 15 of the crotch portion 12 comprises a surface configured for engagement to at least one of the other end segments and a surface configured to be engaged by at least one of the other end segments. At least one of the end segments of the waist portion 14 and the terminal end segment 15 of the crotch portion 12 optionally includes hooks on the surface configured for engagement, and the surface configured to be engaged is configured for engagement by hooks.

The protective undergarment 10 is optionally arranged such that the surface configured for engagement and the surface configured to be engaged on of each of the end segments of the waist and crotch portions 14, 12 are positioned such that the end segments can be engaged in any order. Also, the terminal end segment 15 of the crotch portion 12 of the protective undergarment 10 is optionally narrower than the central segment 13 of the crotch portion 12.

The waist and crotch portions 14, 12 optionally form a substantially "T" shaped configuration when the end segments of the waist and crotch portions 14, 12 are disengaged and the waist and crotch portions 14, 12 are extended. Additionally, the waist portion 14 and crotch portion 12 of the protective undergarment 10 together define leg openings 16 when the terminal end segment 15 of the crotch portion 12 is attached to the waist portion 14, and the protective undergarment 10 optionally includes at least one member 32 for engagement between the crotch portion 12 and the waist portion 14. If used, the engagement member 32 is optionally positioned to adjust the size of at least one of the leg openings. The engagement member 32 is optionally attached to, or extends from, the crotch portion 12 of said protective undergarment 10.

Referring now to FIG. 1, there is shown an exemplary embodiment of the invention, indicated generally at 10, which is configured to be worn by a user (not shown). Undergarment 10 includes a crotch portion 12 and a waist portion 14. The crotch portion 12 has an end segment 11 attached to waist portion 14, a central portion 13, and a detachable or terminal end segment 15, which in this embodiment is narrower in its width than central portion 13. Along the edges of waist portion 14 and central portion 13 there may be elastic borders, indicated at 18.

Located inside the undergarment 10 on crotch portion 12 is a pad retaining portion 21, which in the instant embodiment includes a pair of elastic sleeves 22, although any pad retaining means known in the art may be used. An absorbent pad 24 fits in and under these sleeves 22 and is thus held in place.

Crotch portion engaging means are shown at 26 on waist portion 14, and waist portion engaging means are shown at 28 on terminal end segment 15. Outer leg securing means are shown at 32 on central crotch portion 13, and inner leg securing means are indicated at 30 on waist portion 14. In the embodiment shown, outer leg securing means 32 comprise a hook region 31 surrounded by a region 33 substantially devoid of hooks, but other types of fasteners may be used.

The pad 24 and the entire garment 10 may be disposable, or may be washable and reusable. Alternatively, in the case of a fully disposable undergarment, the pad 24 may be permanently attached to the crotch portion, for example by sewing or via the use of an adhesive, in which case optional elastic sleeves 22 may not be present.

Engaging means 26, 28 and leg securing means 30 and 32 may be any fastener conventionally used in the fastening art for garment applications, including but not limited to adhesives, hooks, or snaps and the like. For example, they may each include a surface carrying hooks and a surface engageable by hooks. Such surfaces include, but are not limited to, woven and non-woven materials comprising polypropylene, polyethylene, polyester, NYLON, or RAYON. Optionally, the hooks may be engageable by loops. Such products are for example available from the Velcro Corporation under the mark VELCRO.

Also optionally, the engaging means may comprise a double-sided fastener wherein there are opposite surfaces, one of which has hooks and the other of which has loops or other material capable of engaging hooks. Incorporating such a feature in two or more locations designed to be attached to each other may allow the user to lay the fastener parts down in a variable sequence, accommodating individual preferences, e.g., for left- or right-handed users.

Additionally, a double-sided fastener may further be constructed such that hooks are positioned in a region to define a border between an edge portion of the fastening means and the hooks, the border being completely or substantially devoid of hooks and the border substantially surrounding said region. Such an arrangement is shown at 32 in FIG. 1 and may, by forming a buffer area around the hook region, reduce unwanted contact of the hook region with the user's skin. Such fasteners may optionally be used for any of the engagement means 26 and 28 and leg securing means 30 and 32. Fastening tabs of this type are disclosed in a co-pending PCT patent application by the same applicant, filed Jul. 15, 2002, and titled DISPOSABLE AND REUSABLE PROTECTIVE UNDERGARMENTS, which is incorporated herein by reference.

The engaging means may be coupled to, or integral with, the structural elements upon which they reside. Although FIG. 1 shows engaging means 26 as a pair of elements, and engaging means 28 and leg securing means 30 and 32 are shown as individual elements, any of these may comprise a single element or a plurality of elements.

Depending on cost, performance requirements, particular uses, and manufacturing considerations, various materials can be selected for use in absorbent articles according to this invention. U.S. Pat. No. 6,004,893 to Van Tilburg, which is incorporated herein by reference, describes a variety of such materials and associated constructions.

For example, absorbent pad 24 may be provided with a topsheet that is liquid permeable and, when the article is in use, is in close proximity to the skin of the user. If used, the topsheet is preferably compliant, soft feeling and non-irritating to the user's skin. Such topsheets can be made from any of the materials conventional for this type of use. Non-limiting examples of suitable materials that can be used as a topsheet are woven and non-woven polyester, polypropylene, polyethylene, NYLON, and RAYON and formed thermoplastic films. Suitable films are described, for example, in U.S. Pat. No. 4,324,246 to Mullane and Smith and U.S. Pat. No. 4,342,314 to Radel and Thompson, both of which patents are incorporated herein by reference. Formed films may be selected for the topsheet because they are pervious to liquids and yet non-absorbent. Thus, the surface of the formed film, which is in contact with the body, remains substantially dry and is more comfortable to the wearer.

If a topsheet is used, its inner surface may be secured in contacting relation to an absorbent core. This contacting relationship results in liquid penetrating the topsheet faster than if it were not in contact with the absorbent core. The topsheet can be maintained in contact with the absorbent core by applying adhesive, optionally in spaced, limited areas, to an inner surface of the topsheet. Examples of suitable adhesives used for this purpose include the acrylic emulsion E-1833BT manufactured by Rohm and Haas Company of Philadelphia, Pa. and acrylic emulsions manufactured by H. B. Fuller Company of St. Paul, Minn. Also contemplated are thermoplastic hot melt adhesives such as 34-563A, available from National Starch, Inc.

Absorbent pad 24 includes an absorbent core that is generally compressible, conformable, and non-irritating to the user's skin. It can comprise any material used in the art for such purpose. Examples of suitable materials are layers of tissue (such as wadding), fibrated comminution pulp (e.g., airfelt), cotton, cellulose acetate, and any of these in combination with a superabsorbent polymer.

Crotch portion 12 preferably comprises a material that is impervious to liquids and thus prevents bodily fluids and feces from soiling the clothing of the user. Any material used in the art for such purposes can be utilized herein. Suitable materials include embossed or non-embossed polyethylene and polypropylene films and laminated tissue and non-woven materials.

Exemplary materials and constructions for reusable absorbent articles are described in U.S. Pat. No. 5,891,122 and U.S. Pat. No. 6,254,583, both issued to Coates, both of which are incorporated herein by reference. Additional materials and constructions are well known in the art of reusable absorbent articles.

FIG. 2 shows the same exemplary embodiment 10 of the invention as in FIG. 1, in a closed conformation such as would be the case when being worn by a user (not shown). Crotch portion 12 has been pulled up so that terminal end segment 15 connects to waist portion 14 at crotch engaging means 26, and outer leg securing means 32 connects to waist portion 14 at inner leg securing means 30 (not shown). The resulting conformation has leg openings 16, in this embodiment bearing optional elastic borders 18.

FIG. 3 shows an exemplary embodiment of the protective undergarment 210 where the outer leg securing means 232 comprise a snap 234 attached to inner leg securing means 230 (not shown), which comprises a complementary snap component.

Figure 4:
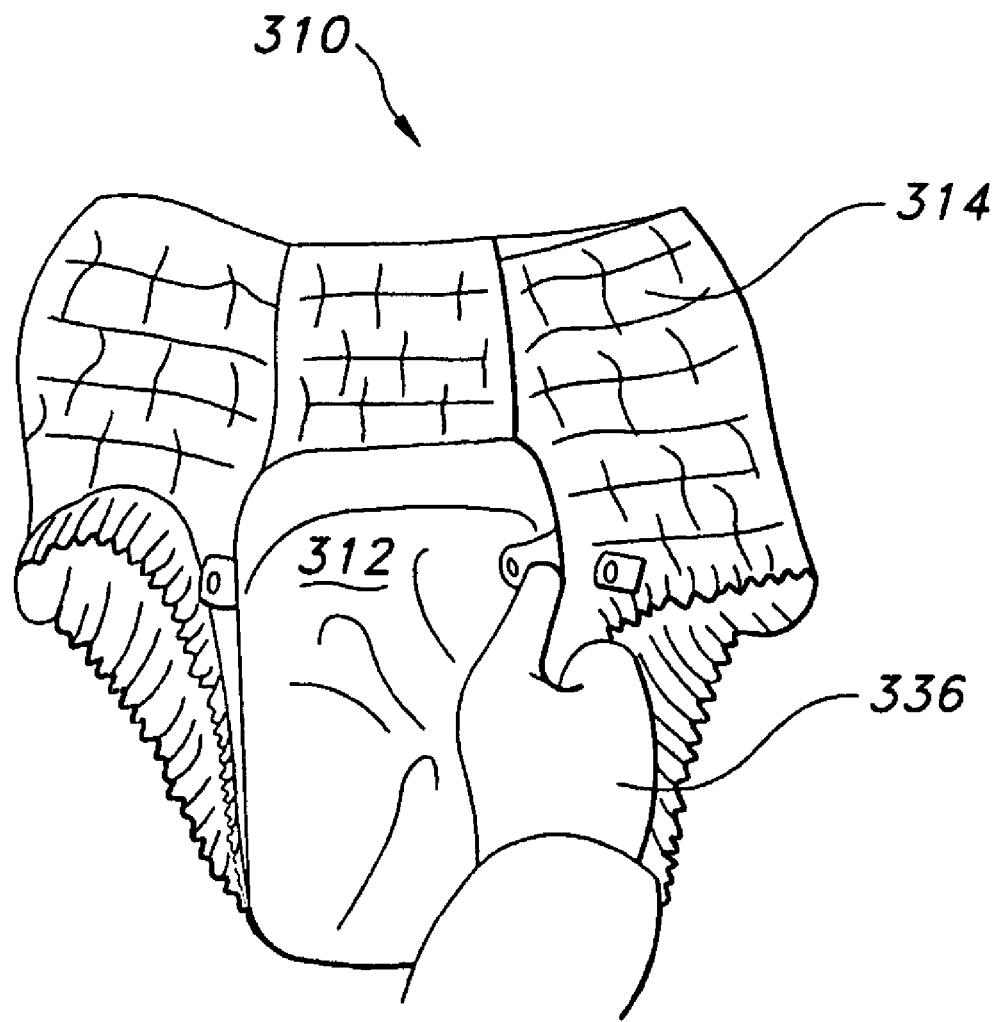
FIG. 4 is a view of still another exemplary embodiment of the invention, as it would be worn, showing a hand positioned to disengage the crotch portion from the waist portion.

FIG. 4 shows an exemplary embodiment of the invention, generally designated by the numeral 310, in closed conformation, with a hand 336 positioned to disengage crotch portion 312 from waist portion 314.

Figure 5:
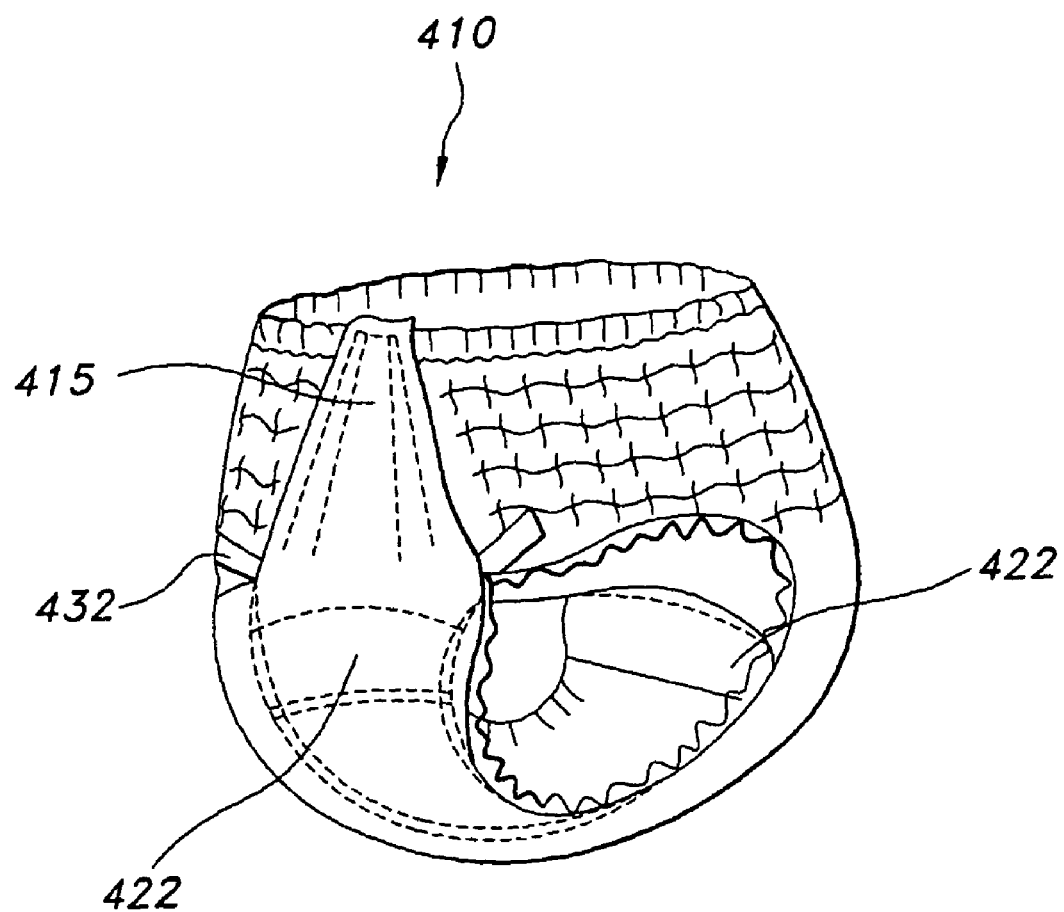
FIG. 5 is a view of yet another exemplary embodiment of the invention, indicating the position of sleeves for retaining an absorbent pad.

FIG. 5 shows another exemplary embodiment of the invention, generally designated by the numeral 410, in closed conformation. Outer leg securing means 432 comprise an adhesive strip, and elastic sleeves designed to hold a detachable absorbent pad (not shown) are indicated at 422.

Figure 6:
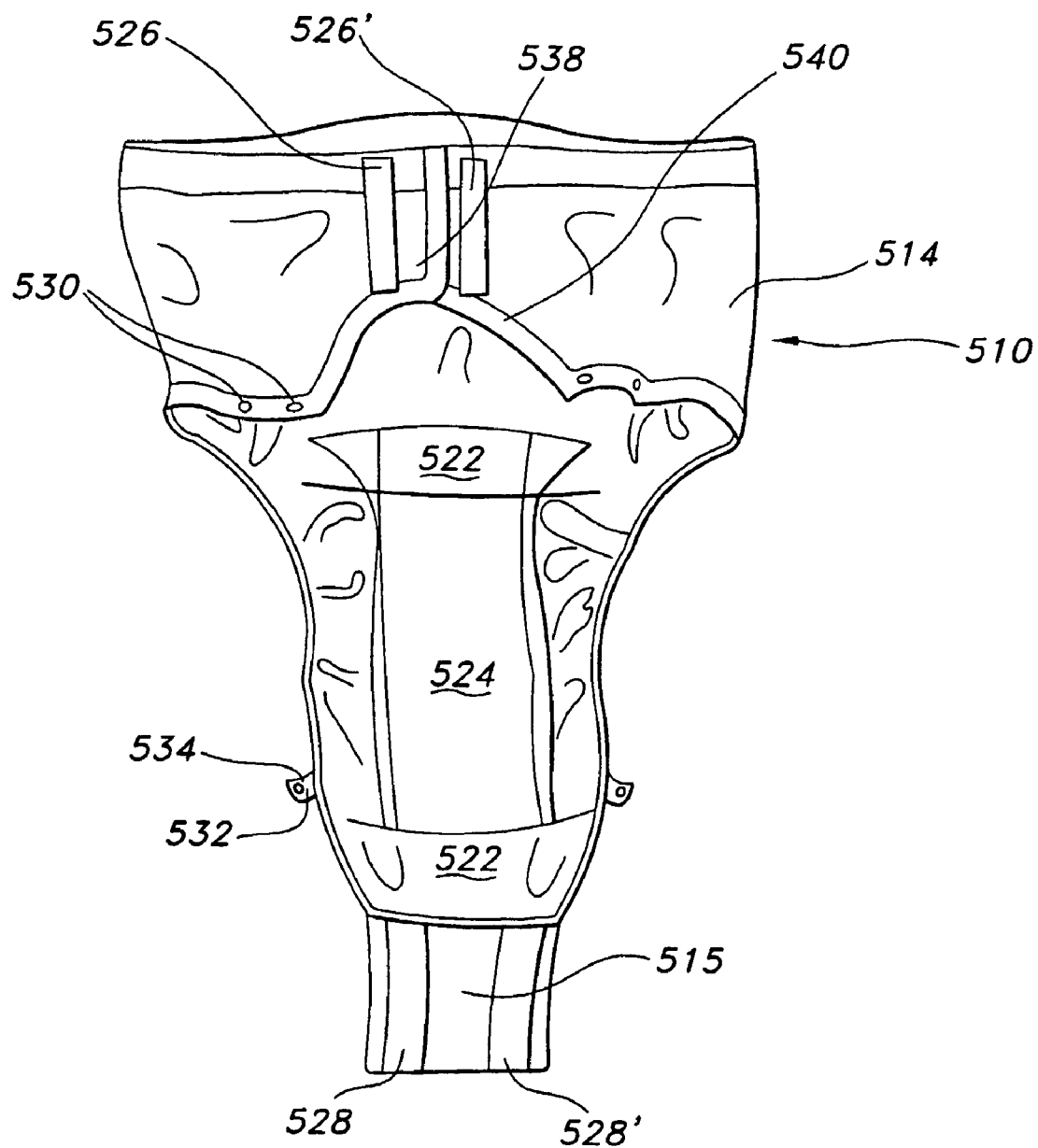
FIG. 6 is a view of another exemplary embodiment of the invention, showing a waist portion that can be opened, and showing the crotch portion opened.

Turning now to FIG. 6, there is shown another embodiment of the invention, generally designated by the numeral 510, in which waist portion 514 comprises first and second end segments 538 and 540, shown here with segment 538 overlapping segment 540. End segment 538 bears a crotch portion engaging means 526 and end segment 540 bears a crotch portion engaging means 526', capable of attaching to waist portion engaging means 528 and 528' respectively on detachable end segment 515. In this embodiment, crotch engaging means 526 comprises a single element, shown here as a strip, while 526' comprises two elements, one of which engages 528' and the other of which (hidden from view) engages the back of segment 538, affording closure of waist portion 514 around the user.

Outer leg securing means 532 bearing snaps 534 are shown in the engaged position with inner leg securing means 530, which in this embodiment includes two snaps on each side to afford adjustability. Although not required, this embodiment comprises elastic sleeves 522 for holding in place absorbent pad 524, which may be disposable or reusable.

Figure 7:
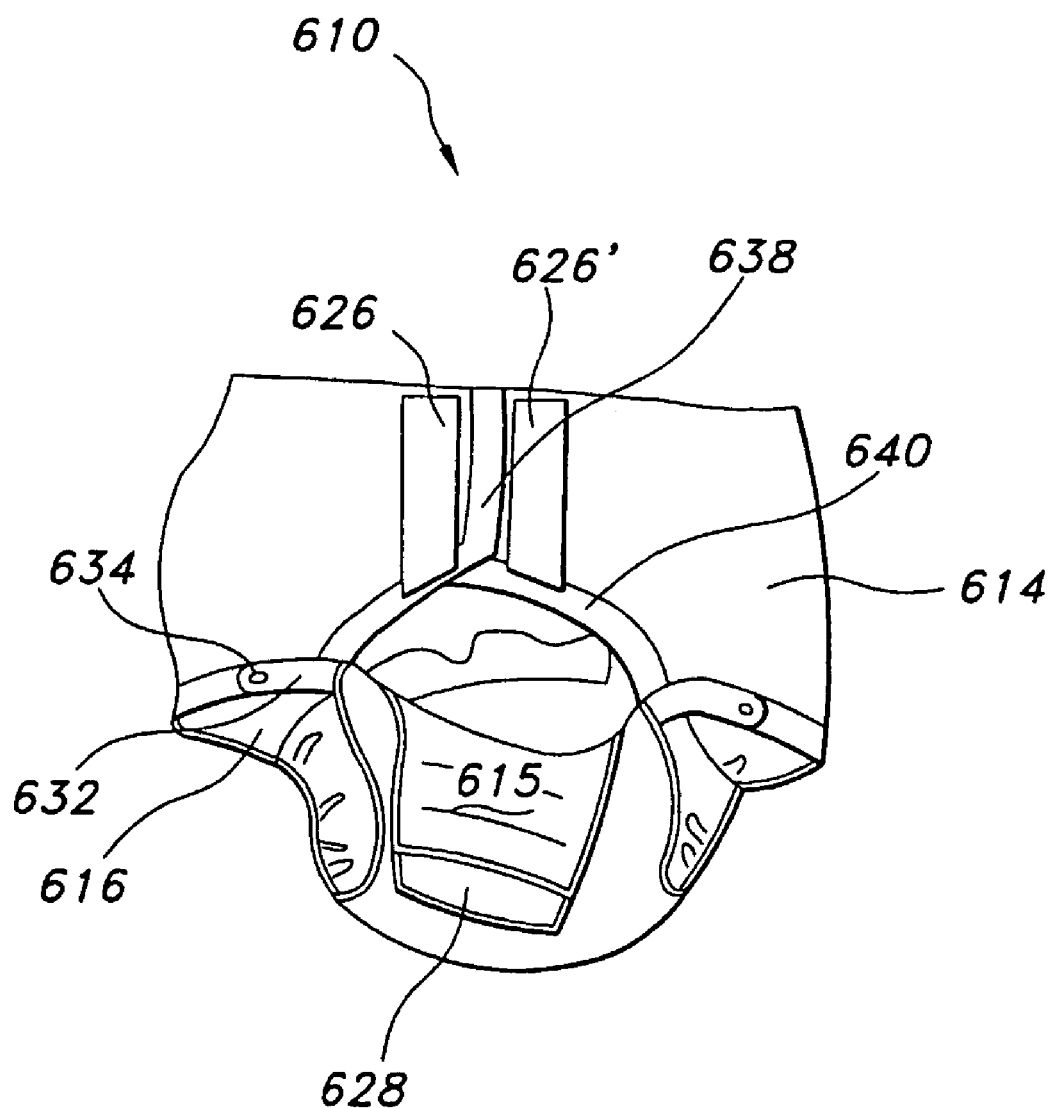
FIG. 7 is a view of an exemplary embodiment of a protective undergarment, according to aspects of the invention, with an openable waist portion, with the crotch portion partially open and leg openings defined by leg securing means comprising snaps.

FIG. 7 shows, with the crotch in partially closed conformation, another exemplary embodiment of the invention, generally designated by the numeral 610, in which waist portion 614 comprises first and second end segments 638 and 640, shown here with segment 638 overlapping segment 640. End segment 638 bears a crotch portion engaging means 626 and end segment 640 bears a crotch portion engaging means 626', both of which are capable of attaching to waist portion engaging means 628, shown here as a single element on detachable end segment 615. In this embodiment, crotch engaging means 626 comprises a single element, shown here as a strip, while 626' comprises two elements, one of which engages 628 and the other of which (hidden from view) engages the back of segment 638, affording closure of waist portion 614 around the user. Outer leg securing means 632 bearing snaps 634 are shown in the engaged position with inner leg securing means 630 (not shown), thereby forming leg holes or openings 616.

Figure 8:
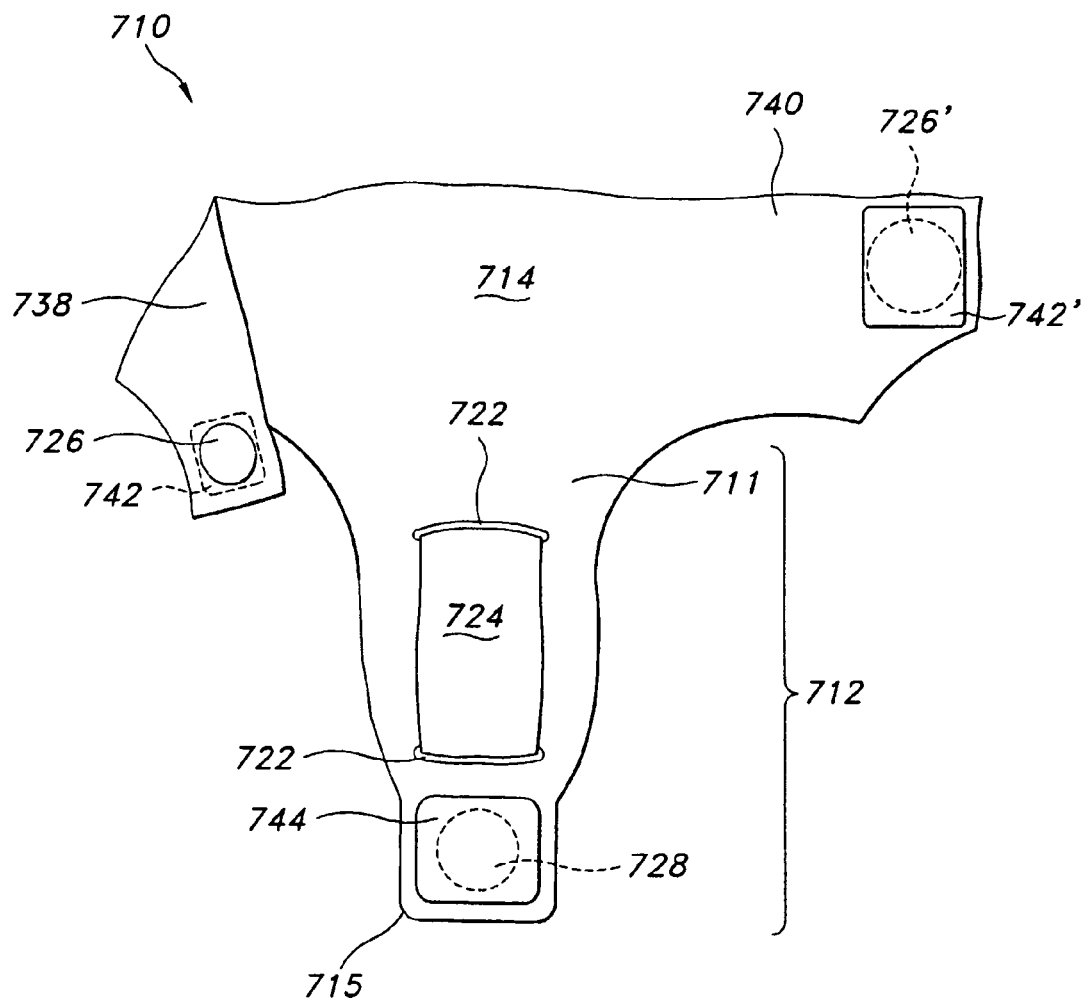
FIG. 8 is a view of another exemplary embodiment of the invention with an open waist portion and the crotch portion disengaged, adapted to allow inter-attachment of two waist portion end segments and a terminal crotch end segment in a common region.

Turning now to FIG. 8, there is shown another exemplary embodiment of the invention, indicated generally at 710. Undergarment 710 includes a crotch portion, generally indicated at 712, and a waist portion 714, which comprises first and second end segments 738 and 740. End segment 738 is shown folded over to reveal features present on the reverse side. Crotch portion 712 has an end segment 711 attached to waist portion 714, a central portion 713, and a detachable end segment 715, which in this embodiment is narrower than central portion 713. Overall, crotch portion 712 extends perpendicular to waist portion 714.

Located inside the undergarment 710 on crotch portion 712 is a pad retaining means 722, which in the instant embodiment is a pair of elastic sleeves 722, although any pad retaining means known in the art may be used. An absorbent pad 724 fits in and under these sleeves 722 and is thus held in place. Pad 724 may be either disposable or reusable.

First and second engaging means are shown at 726 and 726' on end segments 738 and 740 respectively of waist portion 714, and a third engaging means is shown at 728 on detachable end segment 715. In this figure, 726 is shown on top and 726' and 728 are to be understood as out of view, on the far side of undergarment 710. Also shown are first and second engageable means 742 and 742', on end segments 738 and 740 and on the reverse side from engaging means 726 and 726', respectively. Third engageable means 744 is shown on detachable end segment 715, on the reverse side from engaging means 728.

The first, second, and third engaging means 726, 726' and 728, and the corresponding engageable means 742, 742' and 744 may be any fastener conventionally practiced in the fastening art for garment applications, including but not limited to adhesives, hooks, or snaps. In FIG. 8, the first, second and third engaging means comprise hooks, and the first, second and third engageable means comprise loops. Alternatively the engageable means may comprise woven and non-woven materials comprising polypropylene, polyethylene, polyester, NYLON, or RAYON, although this listing is not exclusive or limiting. Advantageously, the hooks may be engageable by loops or by other hooks or by other engageable materials. Such products are for example available from the Velcro Corporation under the mark VELCRO.

Also advantageously, the engaging means may comprise a double-sided fastener wherein there are opposite surfaces, one of which has an engaging surface and the other having a surface engageable by features bearing such an engaging surface. For example, the engaging surface may comprise hooks and the engageable surface may comprise loops or other material capable of engaging hooks. Incorporating such a feature in two or more locations designed to be attached to each other may allow the user to lay the fastener parts down in a variable sequence, accommodating individual preferences, e.g. for left- or right-handed users.

It is recognized that it may be advantageous to orient hooks, if such fastening means are used, so that they face away from the skin of the wearer in order to reduce any discomfort. However, it is also recognized that the hooks or other engagement devices may face the wearer's body.

Additionally, a double-sided fastener may further be constructed such that hooks are positioned in a region to define a border between an edge portion of the fastening means and the hooks, the border being at least partially devoid of hooks and the border substantially surrounding said region. Such an arrangement is shown in FIG. 8, where all of the engaging means 726, 726' and 728 are of a smaller size than the segments 738, 740, and 715, respectively, upon which they reside. Thus a border is created around each of these, thereby reducing unwanted contact of the hook region with the user's skin. Fasteners of this type are disclosed in a co-pending PCT patent application by the same applicant, filed Jul. 15, 2002, and titled DISPOSABLE AND REUSABLE PROTECTIVE UNDERGARMENTS, which is incorporated herein by reference.

The engaging means may be coupled to, or integral with, the structural elements upon which they reside. Although FIG. 8 shows engaging means 726, 726' and 728 as individual elements, any of these may comprise a single element or a plurality of elements. In addition, although FIG. 8 shows the engaging means and the engageable means as circles of smaller size and squares of larger size, respectively, other shapes and sizes of any of these may be used, in any combination. As well, engageable means 742, 742', and 744 may comprise the material of construction of waist portion 714 or crotch portion 712, without attaching separate material for the sake of engageability.

The embodiment shown in FIG. 8 has the advantage that first and second end segments 738 and 740, and detachable end segment 715, can be attached to each other by sequentially laying one on top of the next in any order, such that all three meet in a common region. This may facilitate donning of the garment by a user with limited dexterity.

Figure 9:
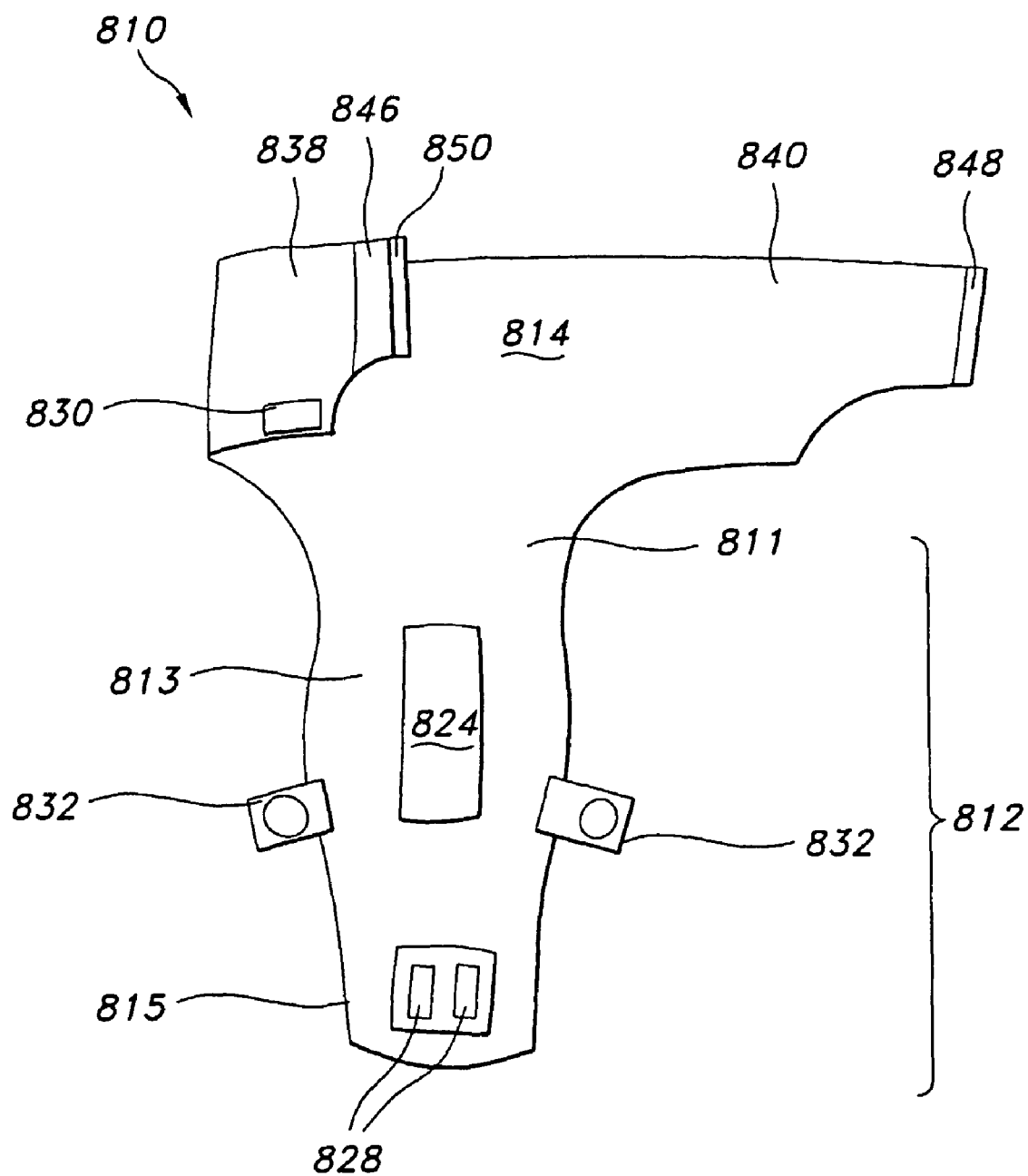
FIG. 9 is a view of still another exemplary embodiment of a protective undergarment according to aspects of the invention.

Turning now to FIG. 9, there is shown another exemplary embodiment of the invention, indicated generally at 810. Undergarment 810 includes a crotch portion generally indicated at 812, and a waist portion 814, which comprises first and second end segments 838 and 840. End segment 838 is shown folded over to reveal features present on the reverse side. Crotch portion 812 has an end segment 811 attached to waist portion 814, a central portion 813, and a detachable end segment 815, which in this embodiment is narrower than central portion 813. Overall, crotch portion 812 extends substantially perpendicular to waist portion 814. An absorbent pad 824 is attached to or integral with crotch portion 812.

End segment 838 comprises a loop area 846 and a hook area 850, the reverse side of which is shown. End segment 840 comprises a loop portion 848, the reverse side of which is shown. Terminal end segment 815 comprises a hook region 828, which is engageable with loop area 846. Crotch portion 812 comprises hook portion 832, which is engageable with loop portion 830.

Figure 9A:
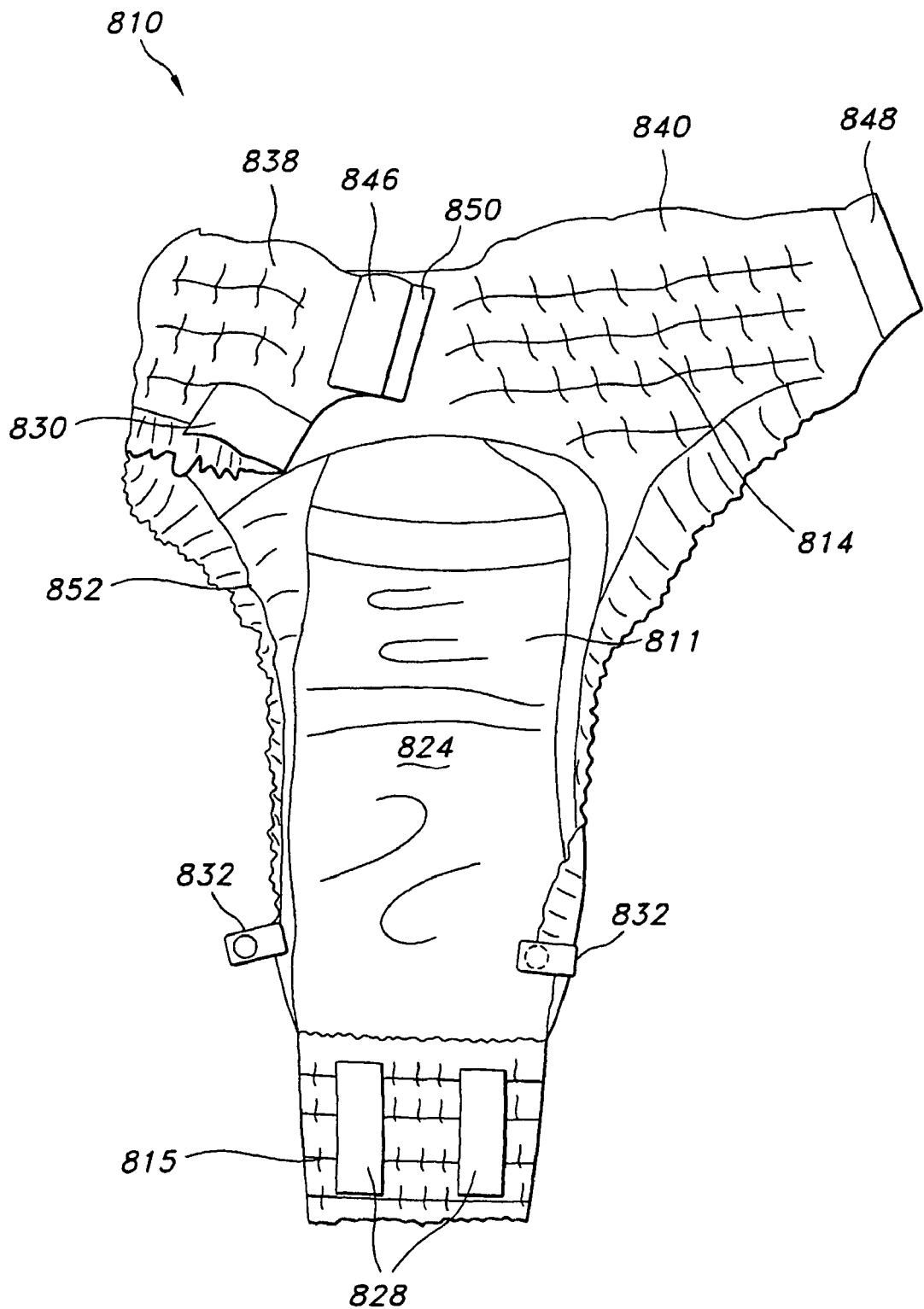
FIG. 9A is another view of the undergarment illustrated in FIG. 9 showing additional exemplary features.

FIG. 9A shows additional details of the protective undergarment 810 shown in FIG. 9. For example, FIG. 9A shows an elastic border 852 along the edges of crotch portion 812 and/or waist portion 814. Also, waist portion 814 may include an elastic material for fit and comfort. Also, further details of the construction of the undergarment 810 are shown.

Figure 10:
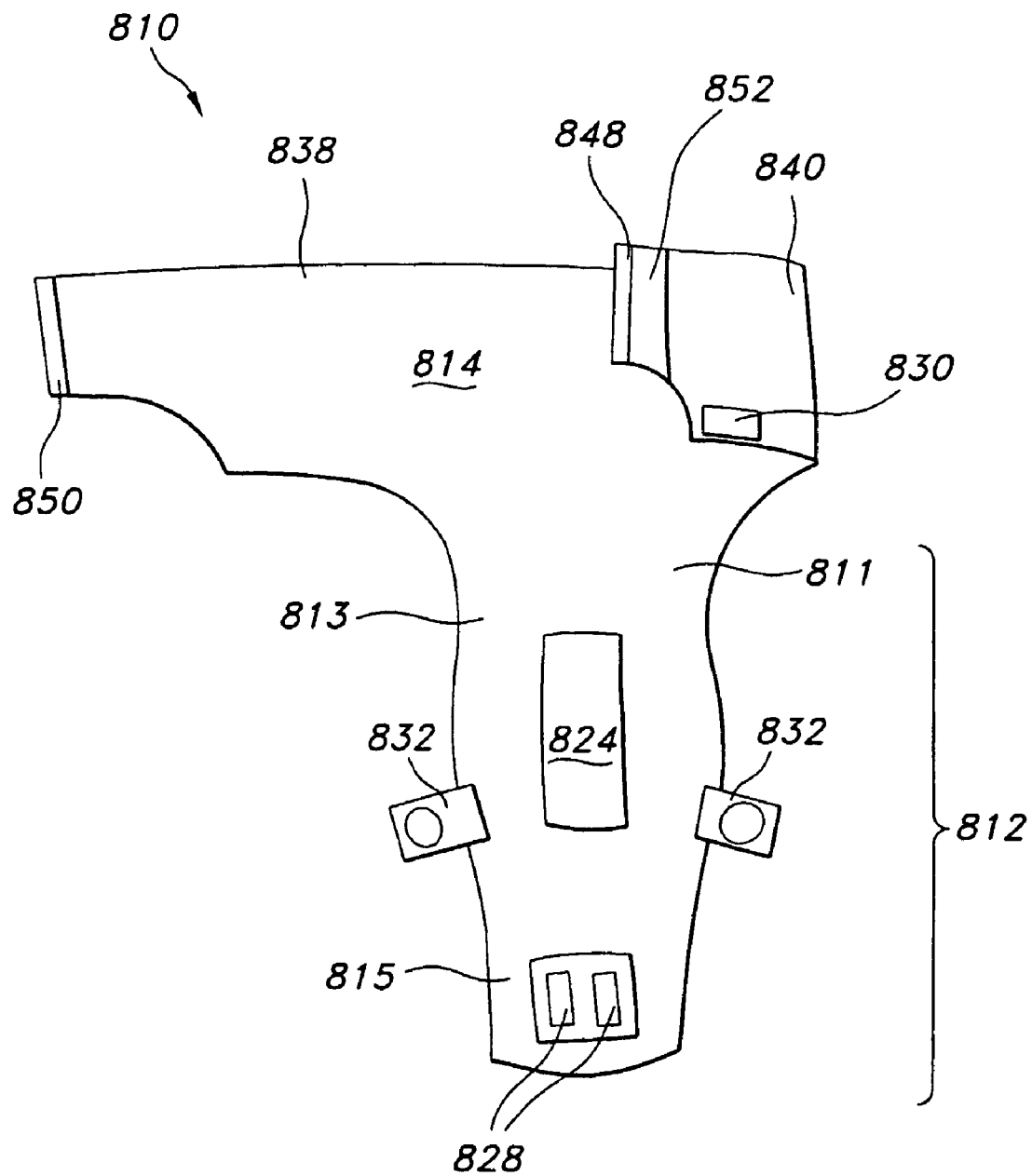
FIG. 10 is another view of the protective undergarment illustrated in FIG. 9.

FIG. 10 is another view of the embodiment shown in FIG. 9, with end segment 838 extended and end segment 940 folded over. There is shown loop area 852 on end segment 840, which is engageable with hook area 828 on terminal end segment 815, and loop area 848, which is engageable with hook area 850 on end segment 838.

Although the invention is illustrated and described herein with reference to specific embodiments, the invention is not intended to be limited to the details shown. Rather, various modifications may be made in the details within the scope and range of equivalents of the claims and without departing from the invention. For example, although certain embodiments disclosed herein are configured for reusable applications, the features of those embodiments apply equally to disposable products. Likewise, although certain embodiments disclosed herein are configured for disposable applications, the features of those embodiments apply equally to reusable products.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention. Having described the invention, we now claim the following and their equivalents.

What is claimed is:

1. A protective undergarment comprising:
   a waist portion adapted to encircle the waist of a user, wherein said waist portion comprises end segments; and
   a crotch portion comprising an end segment extending from said waist portion, a central segment, and a terminal end segment attachable to said waist portion, said terminal end segment extending substantially perpendicular to said waist portion;
   wherein each of said end segments of said waist portion and said terminal end segment of said crotch portion comprises a body facing surface positionable against the body of the user and a surface opposite said body facing surface;
   a fastener positioned on said body facing surface of each waist portion end segment and the terminal end segment;
   a fastener positioned on said opposite surface of each waist portion end segment and the terminal end segment;
   each fastener positioned on said opposite surface being configured for engagement to a fastener positioned on said body facing surface of at least one of said other end segments, and each fastener positioned on said body facing surface being configured to be engaged by a fastener positioned on said opposite surface of at least one of said other end segments; and
   wherein said fasteners of said body facing surface and said fasteners of said opposite surface are positioned such that said end segments and said terminal end segment are configured to be engaged in any order.

2. The protective undergarment of claim 1 wherein, upon engagement, said fasteners of said end segments of said waist portion and said terminal end segment of said crotch portion engage one another in a common region.

3. The protective undergarment of claim 2 wherein, upon engagement, said fasteners of said end segments of said waist portion and said terminal end segment of said crotch portion overlap one another in said common region.

4. The protective undergarment of claim 2, wherein said waist and crotch portions form a substantially "T" shaped configuration when said end segments of said waist and crotch portions are disengaged and said waist and crotch portions are extended.

5. The protective undergarment of claim 1 wherein at least one of said fasteners positioned on said opposite surface comprises hooks configured for engagement, and at least one of said fasteners positioned on said body facing surface is configured for engagement by hooks.

6. The protective undergarment of claim 1 wherein each of said fasteners positioned on said opposite surface comprise hooks configured for engagement, and each of said fasteners positioned on said body facing surface is configured for engagement by hooks.

7. The protective undergarment of claim 1 wherein the fasteners of said end segments of said waist portion are configured for engagement to one another, and the fasteners of said terminal end segment and said end segments of said waist portion are configured for engagement to one another.

8. The protective undergarment of claim 1 wherein said terminal end segment of said crotch portion is narrower than said central segment of said crotch region.

9. The protective undergarment of claim 1 wherein, upon engagement, said fasteners of said end segments of said waist portion and said terminal end segment of said crotch portion engage one another in a common region; and
   wherein said terminal end segment of said crotch portion is narrower than said central segment of said crotch portion.

10. The protective undergarment of claim 1, said waist portion and said crotch portion together defining leg openings when said terminal end segment of said crotch portion is attached to said waist portion, said protective undergarment further comprising at least one member for engagement between said crotch portion and said waist portion, said engagement member being positioned to adjust the size of at least one of said leg openings.

11. The protective undergarment of claim 10, said protective undergarment comprising an engagement member positioned to adjust the size of each of said leg openings.

12. The protective undergarment of claim 10, said engagement member extending from said crotch portion of said protective undergarment.

13. A protective undergarment comprising:
   a waist portion adapted to encircle the waist of a user, wherein said waist portion comprises end segments;
   a crotch portion comprising an end segment extending from said waist portion, a central segment, and a terminal end segment attachable to said waist portion, said terminal end segment extending substantially perpendicular to said waist portion, wherein said terminal end segment of said crotch portion is no wider than said central segment;
   wherein each of said end segments of said waist portion and said terminal end segment of said crotch portion comprises a body facing surface positionable against the body of the user and a surface opposite said body facing surface;
   a fastener positioned on said body facing surface of each end waist portion segment and the terminal end segment;
   a fastener positioned on said opposite surface of each end waist portion segment and the terminal end segment;
   each fastener positioned on said opposite surface being configured for engagement to a fastener positioned on said body facing surface of at least one of said other end segments, and each fastener positioned on said body facing surface being configured to be engaged by a fastener positioned on said opposite surface of at least one of said other end segments; and
   wherein, upon engagement, said end segments of said waist portion and said terminal end segment of said crotch portion engage one another in a common region; and
   wherein said fasteners of said body facing surface and said fasteners of said opposite surface are positioned such that said end segments and said terminal end segment are configured to be engaged in any order.

14. The protective undergarment of claim 13 wherein each of said fasteners of said opposite surface comprise hooks configured for engagement, and each of said fasteners of said body facing surface is configured for engagement by hooks.

15. The protective undergarment of claim 13 wherein fasteners of said end segments of said waist portion are configured for engagement to one another, and said fasteners of said terminal end segment of said crotch portion and said end segments of said waist portion are configured for engagement to one another.

16. The protective undergarment of claim 13, wherein said waist and crotch portions form a substantially "T" shaped configuration when said end segments of said waist and crotch portions are disengaged and said waist and crotch portions are extended.

* * * * *